United States Patent
Utech et al.

(10) Patent No.: US 11,087,866 B2
(45) Date of Patent: Aug. 10, 2021

(54) VARIABLE DOSE DISPENSING SYSTEM

(71) Applicant: CareFusion 303, Inc., San Diego, CA (US)

(72) Inventors: Thomas Utech, Dallas, TX (US); Kim E. Davis, San Diego, CA (US); Maria C. Jaskela, San Rafael, CA (US)

(73) Assignee: CAREFUSION 303, INC., San Diego, CA (US)

( * ) Notice: Subject to any disclaimer, the term of this patent is extended or adjusted under 35 U.S.C. 154(b) by 373 days.

(21) Appl. No.: 15/804,100

(22) Filed: Nov. 6, 2017

(65) Prior Publication Data

US 2018/0060528 A1 Mar. 1, 2018

Related U.S. Application Data

(62) Division of application No. 15/134,962, filed on Apr. 21, 2016, now Pat. No. 9,842,196, which is a division
(Continued)

(51) Int. Cl.
*G16H 20/13* (2018.01)
*G06F 17/00* (2019.01)
(Continued)

(52) U.S. Cl.
CPC ............ *G16H 20/13* (2018.01); *G05B 15/02* (2013.01); *G06F 17/00* (2013.01); *G07F 17/0092* (2013.01); *G16H 40/20* (2018.01)

(58) Field of Classification Search
CPC ........ G16H 20/13; G16H 40/20; G05B 15/02; G07F 17/0092; G06F 17/00
(Continued)

(56) References Cited

U.S. PATENT DOCUMENTS

| 4,653,010 A | 3/1987 | Figler et al. |
| 5,208,762 A | 5/1993 | Charhut et al. |

(Continued)

FOREIGN PATENT DOCUMENTS

| CN | 102483773 A | 5/2012 |
| EP | 1656988 A1 | 5/2006 |

(Continued)

OTHER PUBLICATIONS

U.S. Department of Health and Human Services, Food and Drug Administration, Approved Drug Products with Therapeutic Equivalence Evaluations, 2012, 32nd edition (Year: 2012).*
(Continued)

*Primary Examiner* — Michael Tomaszewski
(74) *Attorney, Agent, or Firm* — Morgan, Lewis & Bockius LLP

(57) ABSTRACT

A variable dose dispensing system may include a processor and memory. The processor may receive a request for a variable dose order of a medication, such as from a user. The processor may request an amount of the medication to be administered, and receive, in response to the request, an indication of the amount to be administered. The processor may verify that the amount to be administered is within a range of the variable dose order. The processor may determine an item in a local inventory that contains at least the amount of the medication to be administered, and may dispense the item. If an amount of the dispensed item exceeds the amount to be administered, such as by a waste amount, the processor may display an indication of the waste amount to the user, and may transmit a notification of the waste amount, such as to a management server.

20 Claims, 7 Drawing Sheets

Related U.S. Application Data of application No. 13/754,724, filed on Jan. 30, 2013, now Pat. No. 9,342,484.

(51) Int. Cl.
| | |
|---|---|
| *G07F 17/00* | (2006.01) |
| *G16H 40/20* | (2018.01) |
| *G05B 15/02* | (2006.01) |

(58) Field of Classification Search
USPC .......................................................... 705/2–3
See application file for complete search history.

(56) References Cited

U.S. PATENT DOCUMENTS

| | | | |
|---|---|---|---|
| 5,991,728 A | 11/1999 | DeBusk et al. | |
| 6,202,923 B1 | 3/2001 | Boyer et al. | |
| 6,317,719 B1 | 11/2001 | Schrier | |
| 7,111,780 B2 | 9/2006 | Broussard et al. | |
| 7,119,689 B2* | 10/2006 | Mallett ................... | G16H 40/20 340/572.1 |
| 7,349,858 B1 | 3/2008 | McGrady et al. | |
| 7,734,478 B2 | 6/2010 | Goodall et al. | |
| 7,734,483 B1* | 6/2010 | Smith ..................... | G16H 70/40 705/3 |
| 7,860,724 B2 | 12/2010 | Chudy et al. | |
| 8,195,328 B2 | 6/2012 | Mallett et al. | |
| 8,280,550 B2 | 10/2012 | Levy | |
| 8,560,345 B2 | 10/2013 | Wehba | |
| 8,655,751 B2 | 2/2014 | Renz | |
| 8,688,468 B1 | 4/2014 | daCosta | |
| 8,827,639 B2 | 9/2014 | Beers et al. | |
| 9,342,484 B2 | 5/2016 | Utech et al. | |
| 10,210,313 B2 | 2/2019 | Utech | |
| 2002/0013640 A1 | 1/2002 | Phoon et al. | |
| 2002/0143434 A1 | 10/2002 | Greeven | |
| 2002/0198624 A1 | 12/2002 | Greenwald et al. | |
| 2003/0189058 A1 | 10/2003 | Liff et al. | |
| 2003/0195654 A1 | 10/2003 | Spano | |
| 2004/0078231 A1 | 4/2004 | Wilkes | |
| 2004/0088187 A1 | 5/2004 | Chudy et al. | |
| 2004/0138921 A1* | 7/2004 | Broussard .............. | G16H 20/13 705/2 |
| 2005/0065820 A1 | 3/2005 | Mallett et al. | |
| 2006/0149416 A1 | 7/2006 | Mohapatra et al. | |
| 2006/0200369 A1 | 9/2006 | Batch et al. | |
| 2006/0249423 A1 | 11/2006 | Reijonen | |
| 2008/0195246 A1 | 8/2008 | Khan et al. | |
| 2008/0195416 A1 | 8/2008 | Khan et al. | |
| 2008/0313103 A1* | 12/2008 | Burns ................ | G06Q 30/0283 705/400 |
| 2009/0012813 A1 | 1/2009 | Berzansky et al. | |
| 2009/0125336 A1* | 5/2009 | Wehba ................... | G06Q 10/00 705/3 |
| 2009/0272677 A1 | 11/2009 | Mallett et al. | |
| 2010/0042437 A1 | 2/2010 | Levy et al. | |
| 2010/0094653 A1 | 4/2010 | Tribble et al. | |
| 2010/0161113 A1 | 6/2010 | Tribble et al. | |
| 2010/0174552 A1 | 7/2010 | Hawkes et al. | |
| 2010/0241270 A1 | 9/2010 | Eliuk et al. | |
| 2011/0010196 A1 | 1/2011 | Nee et al. | |
| 2011/0184751 A1 | 7/2011 | Holmes | |
| 2012/0173254 A1 | 7/2012 | Korhnak et al. | |
| 2012/0185277 A1 | 7/2012 | Tribble et al. | |
| 2012/0239422 A1 | 9/2012 | Chudy et al. | |
| 2012/0323602 A1 | 12/2012 | Ryan et al. | |
| 2013/0018356 A1 | 1/2013 | Prince et al. | |
| 2013/0262138 A1 | 10/2013 | Jaskela et al. | |
| 2014/0156294 A1 | 6/2014 | Tribble et al. | |
| 2014/0180475 A1 | 6/2014 | Paradissis et al. | |

FOREIGN PATENT DOCUMENTS

| | | |
|---|---|---|
| KR | 20120070045 A | 6/2012 |
| WO | WO-0023908 A1 | 4/2000 |
| WO | WO-2001015006 A1 | 3/2001 |
| WO | WO 2001139874 | 6/2001 |
| WO | WO-2006060572 A1 | 6/2006 |

OTHER PUBLICATIONS

Omar Vesga, Maria Agudelo, Beatriz E. Salazar, Carlos A. Rodriguez, and Andres F. Zuluaga, Generic Vancomycin Products Fail In Vivo despite Being Pharmaceutical Equivalents of the Innovator, 2010, American Society for Microbiology, p. 3271-3279 (Year: 2010).*

Australian Office Action for Application No. 2014268799, dated Dec. 9, 2019, 3 pages.

Canadian Office Action for Application No. 2899012, dated Dec. 19, 2019, 7 pages.

Chinese Office Action for Application No. 201480041714.5, dated Dec. 27, 2019, 11 pages.

European Office Action for Application No. 14801251.1, dated Dec. 9, 2019, 7 pages.

United Arab Emirates Office Action for Application No. UAE/P/0956/2015, first received Dec. 12, 2019, 18 pages.

United Arab Emirates Office Action for Application No. UAE/P/1560/2015 from KIPO, first received Nov. 20, 2019, 11 pages.

"Dose Edge Pharmacy Workflow Manager," Baxter International Inc., visited May 21, 2015, retrieved from <https://btsp.baxa.com/doseedge>.

International Search Report and Written Opinion in PCT Application No. PCT/US2014/038654 dated Oct. 7, 2014, 12 pages.

Anonymous: "Pyxis MedStation TM 4000 System, Console User Guide" In: "Part No. 127157-06", Nov. 1, 2010, Cardianl Health XP055121062, pp. 1-228, p. 21-22, p. 38-61, p. 12-124, p. 157-166, Patent 200, p. 216.

International Search Report and Written Opinion in International Patent Application No. PCT/US2014/012594 dated Jun. 11, 2014, 16 pages.

Extended European Search Report for Application No. 14801251.1, dated Jan. 16, 2017, 8 pages.

International Search Report and Written Opinion for Application PCT/US2014/039228, dated Aug. 22, 2014, 11 pages.

Memo for Mexican Office Action for Application No. MX/a/2015/016010, memo dated Apr. 4, 2017, 3 pages.

Chinese Office Action for Application No. 201480017522.0, dated Mar. 20, 2017, 12 pages.

Mexican Office Action dated Sep. 6, 2017 from Mexican Patent Application No. MX/a/2015/016010, 7 pages.

European Office Action for Application No. 14704442.4, dated Feb. 13, 2019, 8 pages.

Australia Office Action for Application No. 2014268799, dated Mar. 26, 2020, 3 pages.

Canada Office Action for Application No. 2913040, May 20, 2020, 4 pages.

India Office Action for Application No. 2398/KOLNP/2015, dated Mar. 19, 2020, 7 pages.

Australia Office Action for Application No. 2019202932, dated Mar. 3, 2020, 3 pages.

Brazil Office Action for Application No. BR112015018107-4, dated Feb. 19, 2020, 5 pages.

Brazil Office Action for Application No. BR112015028942-8, dated Feb. 12, 2020, 5 pages.

Australian Office Action for Application No. 2019202932, dated Jul. 27, 2020, 4 pages.

India India Office Action for Application No. 4009/KOLNP/2015, dated Jun. 25, 2020, 6 pages.

Australian Decision Issued for Application No. 2014268799, dated Feb. 26, 2021, 24 pages.

Canadian Office Action for Application No. 2899012, dated Mar. 22, 2021, 4 pages.

European Office Action for Application No. 14704442.4, dated Jan. 20, 2021, 5 pages.

(56) References Cited

OTHER PUBLICATIONS

Australian Office Action for Application No. 2020205335, dated Mar. 30, 2021, 4 pages.

* cited by examiner

VARIABLE DOSE DISPENSING SYSTEM

CROSS-REFERENCE TO RELATED APPLICATIONS

The presented application is a divisional of pending U.S. patent application Ser. No. 15/134,962 entitled "VARIABLE DOSE DISPENSING SYSTEM," filed on Apr. 21, 2016, now U.S. Pat. No. 9,842,196, issued Dec. 12, 2017, which is a divisional of U.S. patent application Ser. No. 13/754,724 entitled "VARIABLE DOSE DISPENSING SYSTEM," filed on Jan. 30, 2013, now U.S. Pat. No. 9,342,484, issued May 17, 2016, the disclosures of which are hereby incorporated by reference in their entirety for all purposes.

TECHNICAL FIELD

The present description relates generally to dispensing, and more particularly, but not exclusively, to variable dose dispensing.

BACKGROUND

Healthcare facilities, such as hospitals, may utilize medication dispensing devices, such as automated dispensing machines (ADMs), to provide healthcare professionals with controlled access to medications. For example, a medication dispensing device may be stocked, e.g by a pharmacy, with multiple medications that may each have a variety of different doses and a variety of different forms, e.g. tablet, caplet, etc. A pharmacy will communicate an order for an amount of a medication prescribed for a patient, e.g. 2 milligrams (mg) of morphine, to a medication dispensing device, such as over a network. A healthcare professional, such as a nurse, will authenticate with the medication dispensing device and select the order. The medication dispensing device then physically dispenses the ordered amount of the medication to the healthcare professional. The healthcare professional then administers the dispensed medication to the patient. In some examples, the medication dispensing device may be configured to only dispense to the healthcare professional, and/or to only provide the healthcare professional with physical access to, the amount of the medication that was prescribed. In this manner, the amount of wasted medication is substantially minimized and the healthcare facility can control the healthcare professional's access to the medication.

However, in some instances an order received from a pharmacy may be for a variable dose of a medication, e.g. a range of 2-10 mg of morphine. In this instance, the medication dispensing device may allow the healthcare professional to select the medication item(s) that they would like to access, and the medication dispensing device may grant the healthcare professional with access to the selected medication item(s) so long as the total amount of the medication being dispensed is within the range of the order, e.g. within the range of 2-10 mg for the current example. However, if there are a variety of different forms and/or amounts of the medication in the medication dispensing device, it may be confusing and tedious for a healthcare professional to select which of the various medication items they should access to minimize waste, e.g. one 5 mg vial and one 2 mg vial for a 7 mg dose, etc. Furthermore, the healthcare facility's ability to discretely control the healthcare professional's access to the medications may be significantly reduced for variable dose orders, since the healthcare professional may be able to access more medication than they will be administering to the patient.

SUMMARY

The disclosed subject matter relates to a method for variable dose dispensing. The method may include receiving a request for a variable dose order of a medication, requesting an amount of the medication to be administered, and receiving, in response to the requesting, an indication of the amount of the medication to be administered. The method may further include determining, by a processor, at least one item of a plurality of items in a local inventory, the at least one item comprising at least the amount of the medication to be administered, and dispensing the at least one item.

The disclosed subject matter also relates to a machine-readable medium embodying instructions that, when executed by a machine, allow the machine to perform a method for managing variable dose dispensing. The method may include receiving, from a medication dispensing device, a user identifier associated with a user, a dispensed amount of a medication, and an amount of the medication to be administered by the user, wherein the dispensed amount exceeds the amount to be administered by a waste amount. The method may further include initiating, in response to the receiving, a timer associated with the user identifier and the medication, and if, before the timer reaches a timeout threshold, an indication is received from a waste device that indicates that the user associated with the user identifier wasted the waste amount of the medication, storing the indication, otherwise storing a notification that the user associated with the user identifier failed to waste the waste amount before the timer reached the timeout threshold.

The disclosed subject matter also relates to a system for managing variable dose dispensing. The system includes one or more processors and a memory including instructions that, when executed by the one or more processors, cause the one or more processors to: provide a list of formulary items, receive a selection of one of the formulary items, receive a first indication of an amount of another of the formulary items that is an equivalency to the one of the formulary items, store a first association between the amount of the another of the formulary items and the one of the formulary items, and transmit the first association to a medication dispensing device.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

Certain features of the subject technology are set forth in the appended claims. However, for purpose of explanation, several embodiments of the subject technology are set forth in the following figures.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be clear and apparent to those skilled in the art that the subject technology is not limited to the specific details set forth herein and may be practiced using one or more embodiments. In one or more instances, well-known structures and components are shown in block diagram form in order to avoid obscuring the concepts of the subject technology.

The subject variable dose dispensing system may allow a healthcare facility, such as a hospital, to minimize the amount of medication wasted when dispensing variable dose orders. In addition, the subject variable dose dispensing system may simplify the dispensing of variable doses for healthcare professionals by determining which items should be used by the healthcare professional to administer an identified amount of a medication. Furthermore, the subject variable dose dispensing system may allow a healthcare facility to discretely control healthcare professionals' access to medications of variable dose orders, and may allow a healthcare facility to rapidly identify when a healthcare professional may have improperly accessed a given medication.

For exemplary purposes, the subject variable dose dispensing system is discussed herein with respect to the dispensing of variable dose medications in a healthcare facility, e.g. hospital. However, the subject variable dose dispensing system is not limited to dispensing variable dose medications in a healthcare facility; the concepts discussed herein are applicable to the dispensing of medications in other environments.

Figure 1:
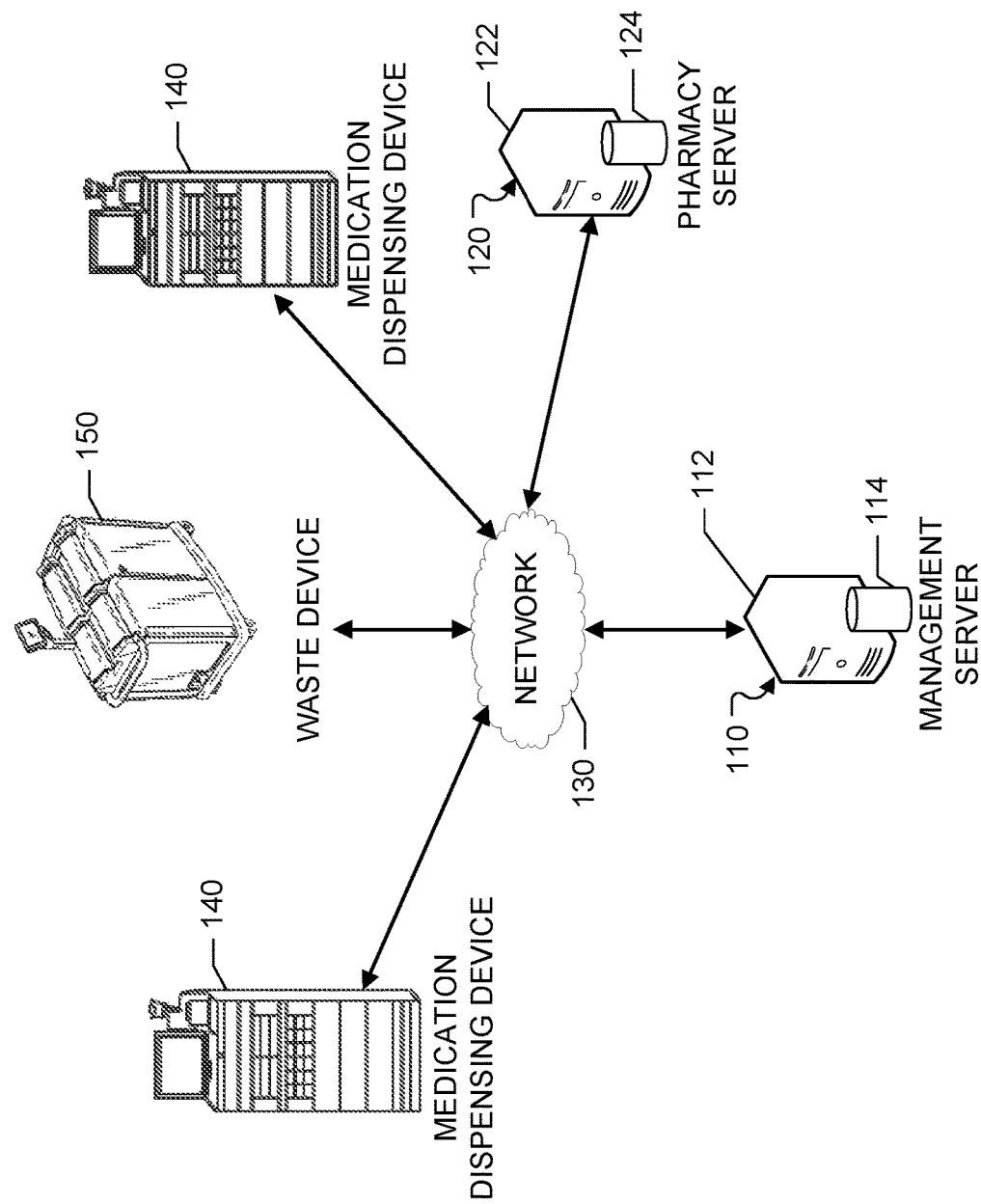
FIG. 1 illustrates an example hospital network environment in which a variable dose dispensing system may be implemented in accordance with one or more embodiments.

FIG. 1 illustrates an example hospital network environment 100 in which a variable dose dispensing system may be implemented in accordance with one or more embodiments. Not all of the depicted components may be required, however, and one or more embodiments may include additional components not shown in the figure. Variations in the arrangement and type of the components may be made without departing from the spirit or scope of the claims as set forth herein. Additional, different or fewer components may be provided.

The network environment 100 may include a number of medical devices, such as one or more medication dispensing devices 140 and/or one or more waste devices 150, that may be communicably coupled to one another and to one or more of a management server 110 and/or a pharmacy server 120, such as by the network 130. In addition, there may be a number of other devices connected to the network 130, such as additional medical devices, additional servers, computing devices, mobile devices, etc.

The network 130 may be a public communication network (such as the Internet, cellular data network, dialup modems over a telephone network) or a private communications network (such as private local area network ("LAN"), leased lines). The network 130 may also include, but is not limited to, any one or more of the following network topologies, including a bus network, a star network, a ring network, a mesh network, a star-bus network, a tree or hierarchical network, and the like. The connections may be wired or wireless.

The one or more medication dispensing devices 140 may be devices that store and dispenses medications, such as at a nurse's station. In one or more embodiments, one or more of the medication dispensing devices 140 may be a Pyxis MedStation™ Automated Dispensing Machine (ADM). The waste devices 150 may be devices that accept and store wasted medications, e.g. excess medications, from healthcare professionals and track the amount of medications wasted by healthcare professionals. In one or more embodiments, one or more of the waste devices 150 may be a Pyxis EcoStation™ system.

In one or more embodiments, one or more of the medication dispensing devices 140 and/or the waste devices 150 may include a processing device, such as a processor, and a memory. The processing device executes computer instructions stored in the memory, such as to implement one or more processes of the subject variable dose dispensing system. In one or more examples, the computer instructions may be stored on a non-transitory computer-readable medium. One or more of the medication dispensing devices 140 and/or the waste devices 150 may be, or may include, the medication dispensing device 600 discussed below with respect to FIG. 6 and/or the electronic system 700 discussed below with respect to FIG. 7. Thus, in one or more embodiments, a medication dispensing device 140 and a waste device 150 may be combined in a single device.

In one example, the management server 110 and/or the pharmacy server 120 may be single computing devices such as computer servers and/or the management server 110 and the pharmacy server 120 may be a single machine. In another example, the management server 110 and/or the pharmacy server 120 may represent one or more separate computing devices (such as a cloud of computers and/or a distributed system) that are communicatively coupled, such as communicatively coupled over the network 130, that collectively, or individually, perform one or more server-side functions. In this example, the one or more computing devices of the management server 110 and/or the pharmacy server 120 may be geographically collocated and/or disparately located. The management server 110 and/or pharmacy server 120 may be coupled with various databases, storage services, or other computing devices.

In one or more embodiments, the management server 110 includes a processing device 112 and a data store 114. The processing device 112 executes computer instructions stored in the data store 114, such as to implement one or more processes of the subject variable dose dispensing system. In one or more examples, the data store 114 may store the computer instructions on a non-transitory computer-readable medium. In one or more embodiments, the pharmacy server 120 includes a processing device 122 and a data store 124. The processing device 122 executes computer instructions stored in the data store 124, such as to implement one or more processes of the subject variable dose dispensing system. In one or more examples, the data store 124 may store the computer instructions on a non-transitory computer-readable medium. In one or more embodiments, the management server 110 and/or the pharmacy server 120 may be, or may include, the electronic system 700 discussed below with respect to FIG. 7.

In operation, one or more of the medication dispensing devices 140 may implement one or more aspects of the subject variable dose dispensing system, such as by performing one or more of the example processes that are discussed further below with respect to FIGS. 2 and 3. In addition, one or more of the management server 110 and/or the pharmacy server 120 may implement one or more aspects of the subject variable dose dispensing system, such as by performing one or more of the example processes that are discussed further below with respect to FIGS. 4 and 5.

Figure 2:
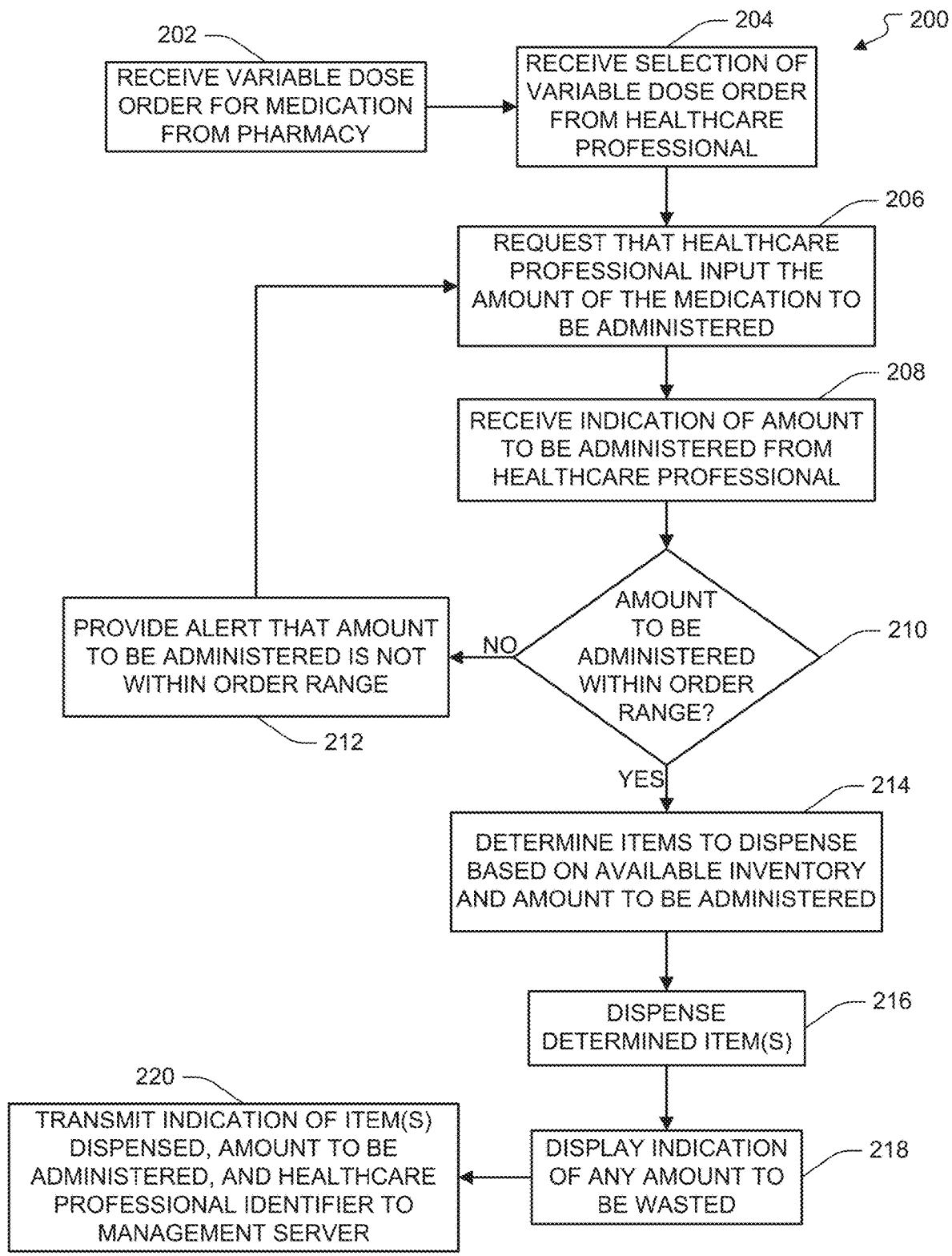
FIG. 2 illustrates a flow diagram of an example process for a medication dispensing device in a variable dose dispensing system in accordance with one or more embodiments.

FIG. 2 illustrates a flow diagram of an example process 200 for a medication dispensing device in a variable dose dispensing system in accordance with one or more embodiments. For explanatory purposes, the example process 200 is described herein with reference to one or more of the devices 140, 150 and/or servers 110, 120 of the example hospital network environment 100 of FIG. 1; however, the example process 200 is not limited to the devices 140, 150 and/or servers 110, 120 of the example hospital network environment 100 of FIG. 1. Further for explanatory purposes, the blocks of the example process 200 are described herein as occurring in serial fashion, or linearly. However, multiple blocks of the example process 200 may occur in parallel. In addition, the blocks of the example process 200 need not be performed in the order shown and/or one or more of the blocks of the example process 200 need not be performed.

In block 202, a medication dispensing device 140 receives a variable dose order from a pharmacy, such as from the pharmacy server 120 over the network 130. In one or more embodiments, the variable dose order may indicate a medication, e.g. one or more medications of the same pure generic name or generic name, and a range of amounts of the medication that may be administered by a healthcare professional to a patient, such as 2-10 mg of morphine. In one or more embodiments, the variable dose order may also include an indication of the dosage form of the medication to be administered, e.g. tablet, caplet, etc. Alternatively, or in addition, the variable dose order may include an identifier of a variable dose group that is associated with the variable dose order, such as a med identifier. In this instance, the variable dose order may or may not indicate a medication, a range, and/or a dosage form. If the variable dose order does not include a range to be administered, the medication dispensing device 140 may use a range and dose unit that is defined for the variable dose order, as discussed further below with respect to FIG. 5.

In block 204, the medication dispensing device 140 receives a selection of a variable dose order from a user, such as a healthcare professional. For example, a healthcare professional may authenticate with the medication dispensing device 140, such as by providing login credentials, and the medication dispensing device 140 may display a list of orders that the healthcare professional is authorized to access. The healthcare professional may then select a variable dose order for a medication from the displayed list, such as a variable dose order for 2-10 mg of morphine every six hours.

In block 206, the medication dispensing device 140 requests that the healthcare professional input the amount of the medication of the variable dose order that will be administered to the patient. In block 208, the medication dispensing device 140 receives an indication of the amount to be administered from the healthcare professional, such as 7 mg of morphine for a 2-10 mg variable dose order of morphine. For example, the healthcare professional may type in an amount to be administered, such as using a keyboard, or may indicate the amount to be administered via a touch screen or other input device. In block 210, the medication dispensing device 140 determines whether the amount of the medication to be administered by the healthcare professional is within the range of the variable dose order. For example, 7 mg of morphine would be within the range of a 2-10 mg variable dose order of morphine, while 11 mg of morphine would not be within the range.

If, in block 210, the medication dispensing device 140 determines that the amount to be administered is not within the range of the variable dose order, the medication dispensing device 140 moves to block 212. In block 212, the medication dispensing device 140 provides an alert to the healthcare professional, such as on a display, an audible alert, or any other alert, that indicates that the amount to be administered is not within the range of the variable dose order. The medication dispensing device 140 then returns to block 206 and requests that the healthcare professional input a different amount to be administered. Alternatively, or in addition, the medication dispensing device 140 may not allow the healthcare professional to input an amount to be administered that is outside of the range of the variable dose order.

If, in block 210, the medication dispensing device 140 determines that the amount to be administered is within the range of the variable dose order, the medication dispensing device 140 moves to block 214. In block 214, the medication dispensing device 140 determines one or more items to dispense based at least in part on the available inventory of the medication dispensing device 140 and the amount of the medication to be administered, e.g. as indicated by the healthcare professional. In one or more embodiments, the medication dispensing device 140 may determine the items to dispense such that the amount of wasted medication from the dispensed items will be minimized. An example process that may be implemented by the medication dispensing device 140 to determine which items to dispense is discussed further below with respect to FIG. 3

In one or more embodiments, the medication dispensing device 140 may receive, e.g. from the pharmacy server 120, an indication of a variable dose group that is associated with the variable dose order. The variable dose group may list the items that can be dispensed by the medication dispensing device 140 to fill the variable dose order. For example, a variable dose group that is associated with variable dose orders for 2-10 mg of morphine may include vials that contain various amounts of morphine, e.g. 2 mg, 5 mg, etc. In this instance, the medication dispensing device 140 may fill a variable dose order by dispensing items that are included in the variable dose group, e.g. such that the amount of wasted medication from the dispensed items will be minimized. The creation of exemplary variable dose groups, and the transmission thereof to medication dispensing devices 140, are discussed further below with respect to FIG. 5.

In block 216, the medication dispensing device 140 dispenses the determined items. In block 218, the medication dispensing device 140 displays an indication of any excess amount of the medication that was dispensed, e.g. any amount of the medication that was dispensed in excess of the amount to be administered. In one or more embodiments, the indication may further include an amount of time that the healthcare professional has to physically waste the excess amount before the excess amount will be identified as missing. In one or more embodiments, the excess amount may be logged as undocumented waste immediately if the user does not waste the excess amount at the time the medication is removed from the medication dispensing device 140. However, the user may still be given an amount of time to physically waste the excess amount before an alert or notification is triggered.

In one or more embodiments, the amount of time that is provided to the healthcare professional to physically waste the excess amount may be based on one or more of: characteristics of the dispensed medication, characteristics of the dosage form of the dispensed medication, characteristics regarding the manner in which the dispensed medication will be administered, and/or characteristics regarding the condition of the patient receiving the dispensed medication. For example, the healthcare professional may be provided with a longer period of time to waste excess medication from a bag of liquid that is to be infused into a patient as compared to a syringe that is to be injected into the patient. In one or more embodiments, the medication dispensing device 140 may determine the amount of time that the healthcare professional has to waste the medication. Alternatively, or in addition, the medication dispensing device 140 may receive the amount of time from a server, such as from the management server 110. In one or more embodiments, the timer may be set to zero if the excess amount is logged as missing if the user does not waste the excess amount at the time the medication is removed from the medication dispensing device 140.

In block 220, the medication dispensing device 140 transmits, such as to the management server 110, the identifier of the healthcare professional, an indication of the one or more items that were dispensed, and at least one of an indication of the amount to be administered and/or an indication of any excess amount that was dispensed. Alternatively, or in addition, if the medication dispensing device 140 determined the amount of time that the healthcare professional has to waste any excess amount of the medication, the medication dispensing device 140 may transmit the amount of time to the management server 110.

Figure 3:
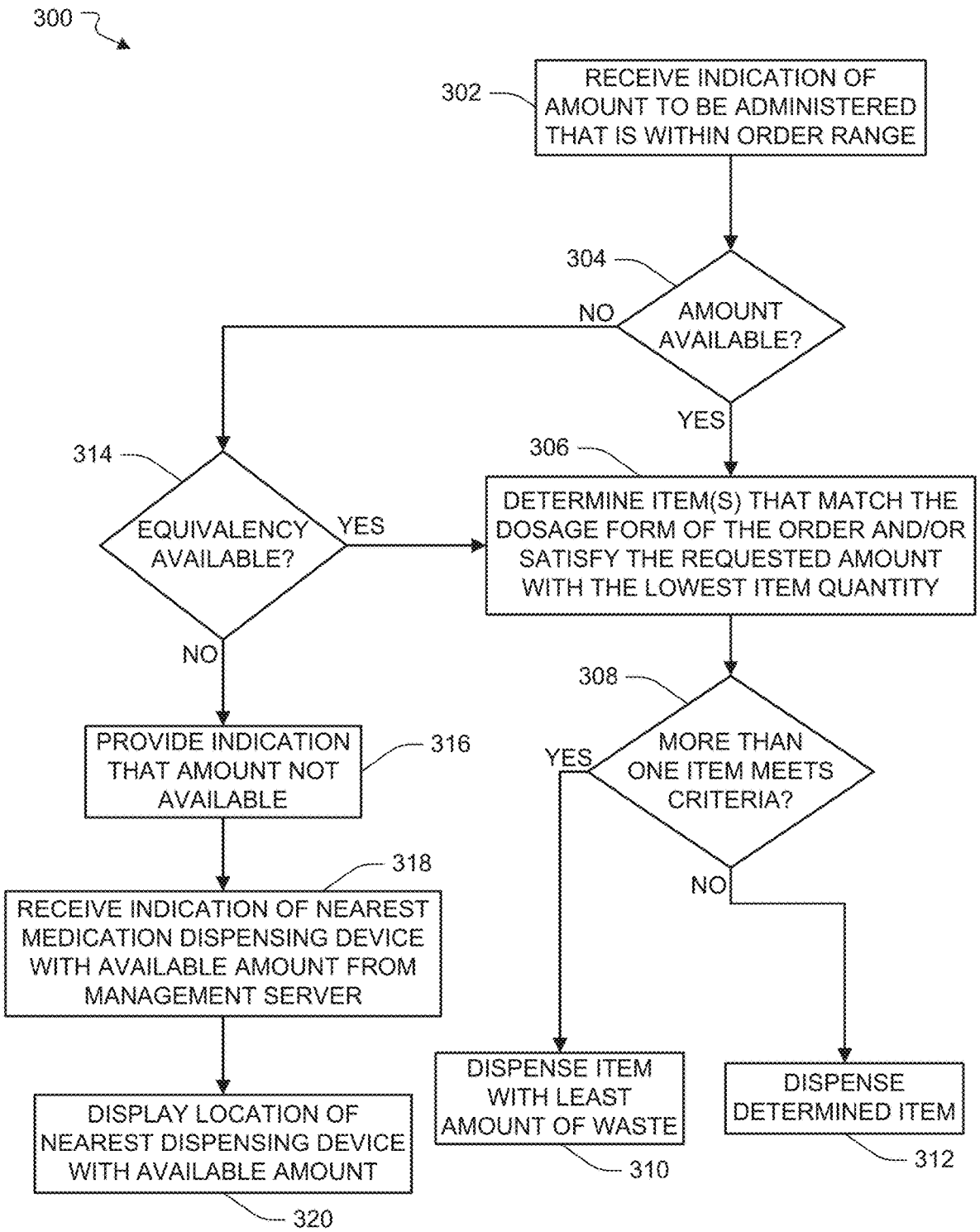
FIG. 3 illustrates a flow diagram of an example item selection process for a medication dispensing device in a variable dose dispensing system in accordance with one or more embodiments.

FIG. 3 illustrates a flow diagram of an example item selection process 300 for a medication dispensing device in a variable dose dispensing system in accordance with one or more embodiments. For explanatory purposes, the example item selection process 300 is described herein with reference to one or more of the devices 140, 150 and/or servers 110, 120 of the example hospital network environment 100 of FIG. 1; however, the item selection process 300 is not limited to the devices 140, 150 and/or servers 110, 120 of the example hospital network environment 100 of FIG. 1. Further for explanatory purposes, the blocks of the example item selection process 300 are described herein as occurring in serial fashion, or linearly. However, multiple blocks of the example item selection process 300 may occur in parallel. In addition, the blocks of the example item selection process 300 need not be performed in the order shown and/or one or more of the blocks of the example item selection process 300 need not be performed.

In block 302, a medication dispensing device 140 receives an indication of an amount of a medication that is to be administered to a patient for a previously selected order, such as a variable dose order. The amount of the medication may have been previously verified as being within a range of the selected variable dose order. Alternatively, or in addition, the selected order may be a zero dose order for a medication that does not contain a range of dispensable amounts. In this instance, the medication dispensing device 140 may dispense any amount of the medication that is requested by a user, such as a healthcare professional.

In block 304, the medication dispensing device 140 determines whether the amount and/or dosage form of the medication to be administered is available in the inventory of the medication dispensing device 140. For example, if the medication dispensing device 140 received a variable dose group that is associated with the variable dose order, the medication dispensing device 140 may determine whether one or more items of the variable dose group are available in inventory that satisfy the amount and/or dosage form of the medication to be administered.

If, in block 304, the medication dispensing device 140 determines that the amount of the medication to be administered is available in the inventory of the medication dispensing device 140, the medication dispensing device 140 moves to block 306. In block 306, the medication dispensing device 140 determines one or more items in inventory that match the dosage form of the variable dose order (or in the same dosage form group) and satisfy the requested amount with the lowest item quantity without splitting the item when the medication dispensing device 140 is configured not to split. For example, a healthcare professional may indicate that 7 mg of morphine will be administered for a variable dose order of 2-10 mg of morphine in vial form, and the medication dispensing device 140 may have two vials of 4 mg, one vial of 8 mg and one vial of 9 mg that are available in inventory. In this example, the two vials of 4 mg of morphine (based on equivalencies as discussed further below), the one vial of 8 mg of morphine, and the one vial of 9 mg of morphine would each satisfy the amount to be administered and be within the range of the variable dose order. However, the one vial of 8 mg of morphine and the one vial of 9 mg of morphine would have a lower item quantity than the two vials of 4 mg of morphine. Thus, in this instance the medication dispensing device would determine that either the one vial of 8 mg of morphine or the one vial of 9 mg of morphine could properly fulfill the order.

In block 308, the medication dispensing device 140 determines whether more than one item, or group of items, meets the criteria used in block 306, e.g. whether more than one item, or group of items, were identified in block 306 as being able to properly fulfilling the order. If, in block 308, the medication dispensing device 140 determines that there is only one item that meets the criteria of block 306, the medication dispensing device 140 moves to block 312. In block 312, the medication dispensing device 140 dispenses the item determined in block 306.

If, in block 308, the medication dispensing device 140 determines that there is more than one item that satisfies the criteria of block 306, such as the 8 mg and 9 mg vials of morphine discussed in the example above, the medication dispensing device 140 moves to block 310. In block 310, the medication dispensing device 140 dispenses the item that will result in the least amount of wasted medication, e.g. the item that has an amount that is closest to the amount to be administered. For example, if the amount to be administered is 7 mg of morphine for a 2 mg-10 mg variable dose order, and the medication dispensing device 140 contains an 8 mg vial and a 9 mg vial, the medication dispensing device 140 dispenses the 8 mg vial since it will only result in 1 mg of waste as opposed to the 2 mg of waste that would result from dispensing the 9 mg vial. Alternatively, or in addition, if more than one item meets the criteria and has the same dosage or in the same dosage form/group, the medication dispensing device 140 may dispense the item with the lowest configured dispense order. In one or more embodiments, the dispense order of the items may be configured by a pharmacy, as is discussed further below with respect to FIG. 5.

If, in block 304, the medication dispensing device 140 determines that the amount to be administered is not available in the inventory, the medication dispensing device 140 moves to block 314. In block 314, the medication dispensing device 140 determines whether the inventory contains equivalencies of the medication for the amount to be administered. For example, the medication dispensing device 140 may receive, from a pharmacy server 120, an indication of one or more items that are equivalencies of another item, e.g. two 2 mg vials of morphine may be indicated as an equivalency of one 4 mg vial of morphine. The creation of exemplary equivalencies, and the transmission thereof to medication dispensing devices 140, are discussed further below with respect to FIG. 5.

Figure 6:
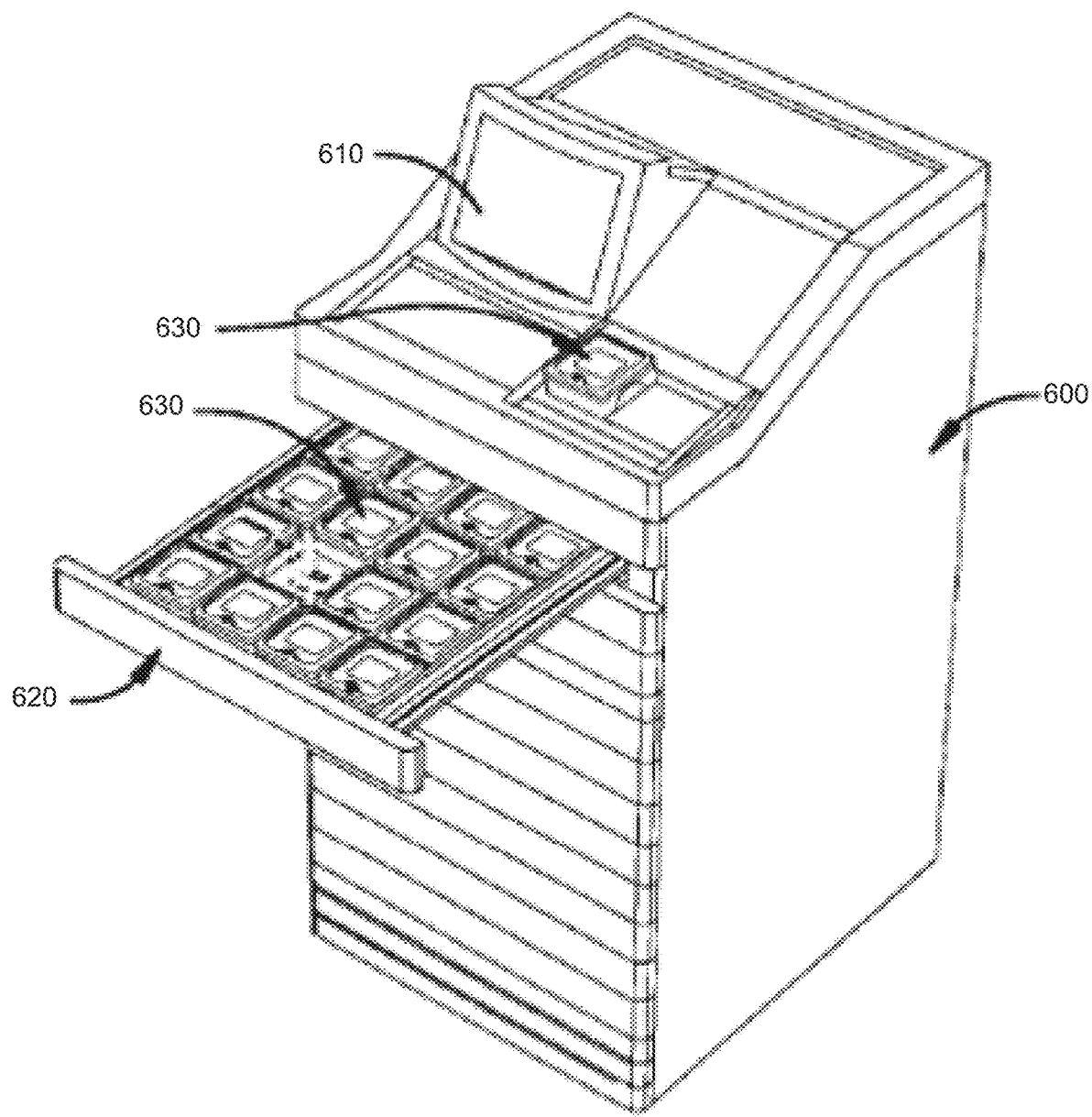
FIG. 6 illustrates an example medication dispensing device that may implement a variable dose dispensing system in accordance with one or more embodiments.

In one or more embodiments, the medication dispensing device 140 may consider an ordered medication's equivalencies when one or more of the following criteria are satisfied: the ordered item results in an invalid amount, e.g. a fractional amount, the ordered item is inactive, the ordered item is not loaded, the ordered item is out of stock, there is insufficient quantity of the ordered item, or there is not indirect access for the healthcare professional based on the drawer that the item is in, as discussed further below with respect to FIG. 6.

If, in block 314, the medication dispensing device 140 determines that the amount to be administered can be provided through one or more equivalencies of the medication, the medication dispensing device 140 moves to block 306. Alternatively, or in addition, the medication dispensing device 140 may perform the equivalencies determination at block 304. In this instance, the medication dispensing device 140 may move directly to block 316 (skipping block 314), if the medication dispensing device 140 determines that the amount to be administered is not available in inventory and can not be provided through equivalencies of the medication. In one or more embodiments, if there are multiple equivalences available, the medication dispensing device 140 may dispense the equivalency that results in no wasted medication and no more than three items dispensed, or that results in the least number of items dispensed.

If, in block 314, the medication dispensing device 140 determines that the amount to be administered can not be provided through equivalencies, the medication dispensing device 140 moves to block 316. In block 316, the medication dispensing device 140 provides an indication that the amount to be administered is not available in the inventory of the medication dispensing device 140. In block 318, the medication dispensing device 140 receives an indication, such as from the management server 110, of the nearest medication dispensing device 140 that can provide the healthcare professional with the amount of the medication to be administered, e.g. in the form of the ordered medication and/or through equivalencies. In block 320, the medication dispensing device 140 displays an indication of the nearest medication dispensing device 140 that can provide the amount to be administered. The medication dispensing device 140 may further display the location of the nearest medication dispensing device 140 that can provide the amount to be administered, such as on a map of the healthcare facility. Alternatively, or in addition, the medication dispensing device 140 may display instructions for navigating to the nearest medication dispensing device 140 that can provide the amount to be administered. In one or more embodiments, the medication dispensing device 140 may also transmit the directions to a mobile device of the healthcare professional, such as over the network 130 or over a local area network connection, e.g. a Bluetooth connection.

Figure 4:
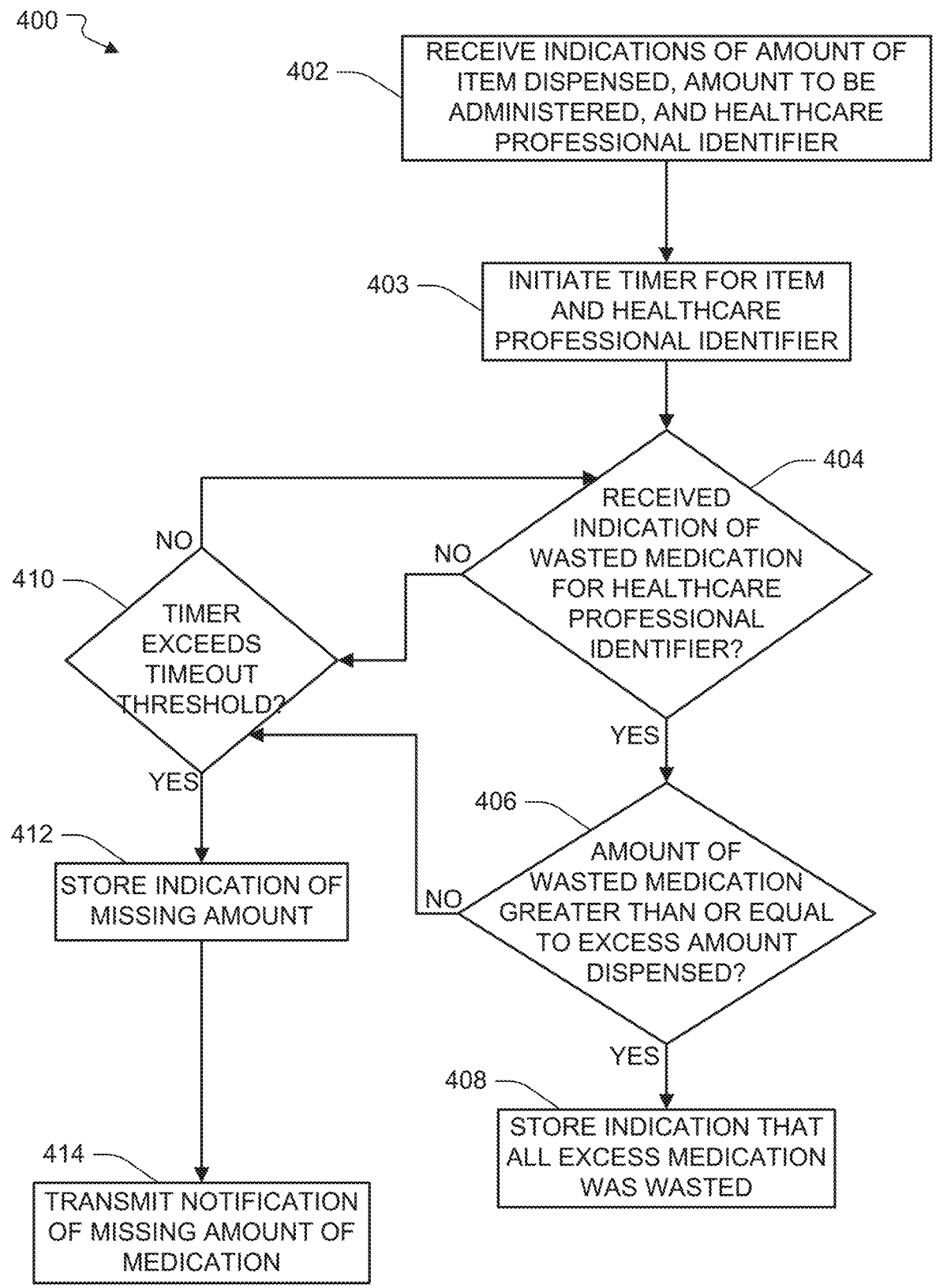
FIG. 4 illustrates a flow diagram of an example item management process in a variable dose dispensing system in accordance with one or more embodiments.

FIG. 4 illustrates a flow diagram of an example item management process 400 in a variable dose dispensing system in accordance with one or more embodiments. For explanatory purposes, the example item management process 400 is described herein with reference to one or more of the devices 140, 150 and/or servers 110, 120 of the example hospital network environment 100 of FIG. 1; however, the example item management process 400 is not limited to the devices 140, 150 and/or servers 110, 120 of the example hospital network environment 100 of FIG. 1. Further for explanatory purposes, the blocks of the example item management process 400 are described herein as occurring in serial fashion, or linearly. However, multiple blocks of the example item management process 400 may occur in parallel. In addition, the blocks of the example item management process 400 need not be performed in the order shown and/or one or more of the blocks of the example item management process 400 need not be performed.

In block 402, a server, such as the management server 110, receives, such as from a medication dispensing device 140, an indication of an amount of a medication that was dispensed to a healthcare professional, an amount that the healthcare professional indicated would be administered, and an identifier of the healthcare professional. In one or more embodiments, the amount that the healthcare professional indicated would be administered may be less than the amount that was dispensed, and the difference between the two may be referred to as an amount to be wasted, a waste amount, or an excess amount. Alternatively, or in addition, the management server 110 may receive an indication of the amount dispensed, the amount to be wasted, and the identifier of the healthcare professional. The management server 110 may store the received information, such as in data store 114. In block 403, the management server 110 initiates a timer with respect to the item dispensed and the user identifier. The management server 110 may utilize the timer to determine when the healthcare professional has exceeded the amount of time allotted for wasting the additional amount of the medication that was dispensed. In one or more embodiments, the management server 110 may concurrently manage multiple timers for the same healthcare professional, e.g. for different medications accessed by the healthcare professional at different times and/or for multiple healthcare professionals.

In block 404, the management server 110 determines whether an indication that the healthcare professional wasted an amount of the medication was received, such as from a waste device 150. For example, a healthcare professional may dispose of an amount of excess medication in a waste device 150. The healthcare professional may provide their login credentials to the waste device 150 such that the waste device 150 can associate the healthcare professional with the amount of the medication that was wasted. In one or more embodiments, the waste device 150 may automatically determine the amount of the medication that was wasted, e.g. by using an item counter, such as a pill counter, by measuring a volume of liquid wasted, by determining a weight of a disposed item and comparing the measured weight to a per unit weight of the disposed item, etc. Alternatively, or in addition, the healthcare professional may input the type of medication and/or the amount of the medication that was wasted. Alternatively, or in addition, the waste device 150 may require that the healthcare professional have a witness while they waste the excess amount, and the witness may also be required to provide their login credentials to the waste device 150.

If, in block 404, the management server 110 determines that the indication has not been received, the management server 110 moves to block 410. In block 410, the management server 110 determines whether the timer exceeds the timeout threshold, e.g the amount of time allotted for the healthcare professional to waste the excess amount of the dispensed medication. If, in block 410, the management server 110 determines that the timer does not exceed the timeout threshold, the management server 110 returns to block 404 and determines whether the indication has been received.

If, in block 410, the management server 110 determines that the timer has exceeded the timeout threshold, the management server 110 moves to block 412. In block 412, the management server 110 stores an indication of the amount of the medication that was not wasted along with the identifier of the healthcare professional. In block 414, the management server 110 transmits a notification that the medication has not been wasted, such as to a supervisor of the healthcare professional, to a security personnel, etc. In one or more examples, the notification may also be transmitted to the medication dispensing devices 140 and may further indicate to the medication dispensing devices 140 that no additional medication should be dispensed to the healthcare professional. Alternatively, or in addition, the notification may be transmitted to an access control system for the healthcare facility and may further indicate to the access control system that the access privileges of the healthcare professional, e.g. via a badge, should be revoked. In this manner the healthcare professional may be prevented from leaving the healthcare facility with the amount of the medication that was not wasted.

If, in block 404, the management server 110 determines that it received the indication that the healthcare professional has wasted an amount of the medication, the management server 110 moves to block 406. In block 406, the management server 110 determines whether the amount that was wasted by the healthcare professional is greater than or equal to the excess amount that was dispensed to the healthcare professional. If, in block 406, the management server 110 determines that the amount the medication that was wasted by the healthcare professional is not greater than or equal to the excess amount of medication, the management server 110 moves to block 410. If, in block 406, the management server 110 determines that the amount of the medication that was wasted by the healthcare professional is equal to or greater than the excess amount of the medication, the management server 110 moves to block 408. In block 408, the management server 110 stores an indication, such as in data store 114, that all of the excess medication that was dispensed to the healthcare professional was wasted by the healthcare professional.

In one or more embodiments, the management server 110 may monitor whether the healthcare professional administered the amount of the medication that the healthcare professional indicated would be administered. For example, the management server 110 may be in communication, over the network 130, with one or more additional medical devices, e.g. dispensing and/or infusion devices, such as pumps. The dispensing and/or infusion devices may transmit an indication to the management server 110 of the amount of the medication that was administered by the healthcare professional to the patient. For example, an infusion pump, or a device coupled thereto, may require that the healthcare professional provide their login credentials before programming the amount of medication that will be infused into the patient. After infusing the medication into the patient, the infusion pump, or a device coupled thereto, may transmit to the management server 110 the amount of the medication that was infused into the patient along with the user identifier of the healthcare professional.

In these one or more embodiments, the management server 110 may transmit the notification of missing medication when the amount of medication administered to the patient is less than the amount that the healthcare professional indicated would be administered. Alternatively, or in addition, the management server 110 may transmit the notification of the missing medication when the amount of the medication administered to the patient plus the amount of wasted medication is less than the amount of the medication dispensed to the healthcare professional. In any of the aforementioned examples, the management server 110 may incorporate one or more thresholds to account for de minimis losses of medication that may occur while the medication is being transported, administered, etc.

Figure 5:
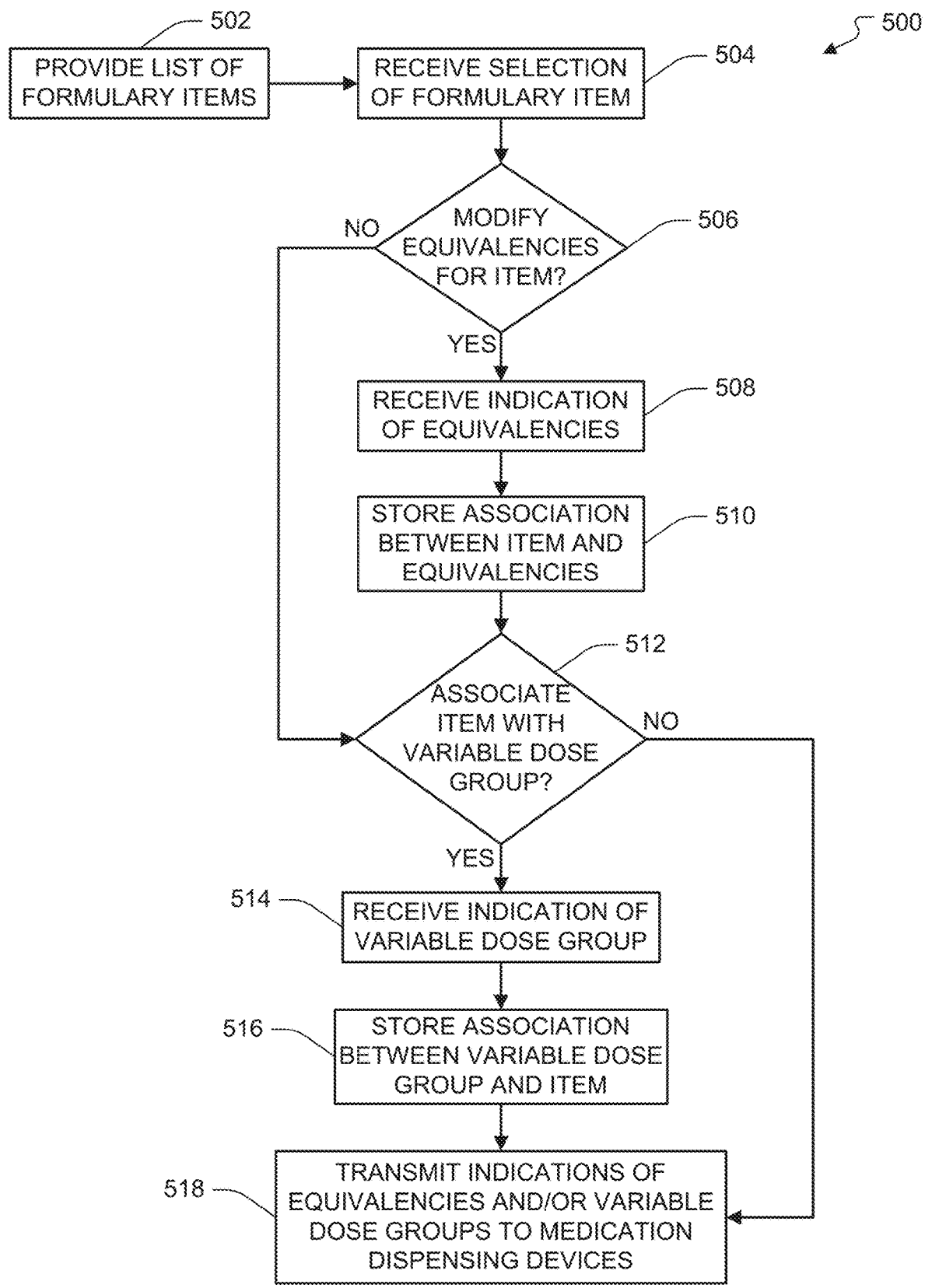
FIG. 5 illustrates a flow diagram of an example item configuration process in a variable dose dispensing system in accordance with one or more embodiments.

FIG. 5 illustrates a flow diagram of an example item configuration process 500 in a variable dose dispensing system in accordance with one or more embodiments. For explanatory purposes, the example item configuration process 500 is described herein with reference to one or more of the devices 140, 150 and/or servers 110, 120 of the example hospital network environment 100 of FIG. 1; however, the example item configuration process 500 is not limited to the devices 140, 150 and/or servers 110, 120 of the example hospital network environment 100 of FIG. 1. Further for explanatory purposes, the blocks of the example item configuration process 500 are described herein as occurring in serial fashion, or linearly. However, multiple blocks of the example item configuration process 500 may occur in parallel. In addition, the blocks of the example item configuration process 500 need not be performed in the order shown and/or one or more of the blocks of the example item configuration process 500 need not be performed.

In block 502, a server, such as the pharmacy server 120, may provide a list of formulary items to a user, such as a pharmacist. For example, a pharmacist may interact with an application, such as a web application, a mobile application, or generally any computing application, provided by the pharmacy server, such as by using a computing device that includes a processor and a memory. In this example, the list of formulary items may be displayed to the user on the computing device. In block 504, the pharmacy server 120 receives a selection of one of the listed formulary items. For example, a user may interact with the application provided by the pharmacy server 120 to select one of the listed formulary items, and the computing device of the user may transmit an indication of the selection to the pharmacy server 120.

In block 506, the pharmacy server 120 determines whether the user has requested to modify or add equivalencies for the selected item. For example, the user may interact with the application provided by the pharmacy server 120 to indicate that they would like to add or modify the equivalencies of the selected item, and the computing device of the user may transmit an indication of the same to the pharmacy server 120. If, in block 506, the pharmacy server 120 determines that the user has requested to modify the equivalencies of the selected item, the pharmacy server 120 moves to block 508. In block 508, the pharmacy server 120 receives an indication of amounts of one or more items in the list of formulary items that are equivalencies of the selected item. For example, the user may interact with the application provided by the pharmacy server 120 to indicate the amounts of one or more items in the list of formulary items that are equivalencies of the selected item, and the computing device of the user may transmit the indicated amounts to the pharmacy server 120.

In one or more embodiments, the pharmacy server 120 may suggest items that may be equivalents to the selected item. For example, each of the formulary items may be associated with a generic name, such as "morphine," and the pharmacy server 120 may suggest items as equivalents that satisfy one or more of the following: have the same generic name as the selected item, have the same dosage form as the selected item, and/or have an equivalency quantity that is below a threshold, e.g. the amount of the item that is equivalent to the selected item. In one or more embodiments, if the selected item is defined by a strength, the pharmacy server 120 may suggest an item that may be an equivalent of a selected item based on one or more of the following: the strength of the item and/or the strength of the selected item, whether the strength of the item is divisible by the strength of the selected item without resulting in fractional amounts, and/or the unit of measure of the item and/or the selected item. In one or more embodiments, if the selected item is defined by a strength and a total volume, the pharmacy server 120 may suggest items as equivalents that have a derived concentration based on the strength and total volume.

In one or more embodiments, if a selected item is defined by a total volume, the pharmacy server 120 may suggest items as equivalents that satisfy one or more of the following: have a total volume, have a volume amount that is divisible into the selected item's without resulting in fractional amounts, and/or have the same unit of volume or same configured base unit as the selected item. In one or more embodiments, if the selected item is defined by a concentration, the pharmacy server 120 may suggest items as equivalents that satisfy one or more of the following criteria: have the same concentration as the selected item, have a concentration strength that is divisible into the selected item's strength without resulting in fractional amounts, have a concentration strength with the same unit of measure or same configured base unit as the selected item, and/or have a concentration volume with a same internal volume or same configured base unit as the selected item.

In block 510, the pharmacy server 120 stores an association between the item and each of the indicated equivalencies, such as in the data store 124. If, in block 506, the pharmacy server 120 determines that the user has not indicated that they would like to modify the equivalencies of the selected item, the pharmacy server 120 moves to block 512. In one or more embodiments, the pharmacy server 120 may remove an item as an equivalency of the selected item if the information that matched the items changes, e.g. the generic name of either item.

In block 512, the pharmacy server 120 determines whether the user has requested to associate the selected item with one or more variable dose groups. For example, the user may interact with the application provided by the pharmacy server 120 to indicate that they would like to associate the selected item with one or more variable dose groups, and the computing device of the user may transmit an indication of the same to the pharmacy server 120. If, in block 512, the pharmacy server 120 determines that the user has requested to associate the selected item with one or more variable dose groups, the pharmacy server 120 moves to block 514.

In block 514, the pharmacy server 120 may receive an indication of one or more variable dose groups that the user would like to associate with the selected item. For example, the user may interact with the application provided by the pharmacy server 120 to indicate the one or more variable dose groups, and the computing device of the user may transmit the indicated variable dose groups to the pharmacy server 120. In block 516, the pharmacy server 120 stores an association between the item and each of the indicated variable dose groups, such as in the data store 124. In one or more embodiments, the user may also associate a dosage range with the variable dose group, such as 2-10 mg.

In block 518, the pharmacy server 120 transmits the equivalencies of the selected item, and/or the variable dose groups associated with the selected item, to one or more medication dispensing devices 140, such as across one or more healthcare facilities. For example, the pharmacy server 120 may transmit the equivalencies and variable dose group associations to one or more of the medication dispensing devices 140 that are stocked by the pharmacy. In one or more embodiments, the pharmacy server 120 may transmit the stored equivalencies and variable dose groups on a periodic basis, such as an hourly basis, a daily basis, a weekly basis, etc. Alternatively, or in addition, the pharmacy server 120 may transmit equivalencies and variable dose groups as they are indicated by a user.

FIG. 6 illustrates an example medication dispensing device 600 that may implement a variable dose dispensing system in accordance with one or more embodiments. Not all of the depicted components may be required, however, and one or more embodiments may include additional components not shown in the figure. Variations in the arrangement and type of the components may be made without departing from the spirit or scope of the claims as set forth herein. Additional, different or fewer components may be provided.

The medication dispensing device 600 may include a display 610 and one or more drawers 620. The one or more drawers 620 may include one or more receptacles 630, that may each contain one or more medication items. The display 610 of the medication dispensing device 600 may be a touch screen and/or the medication dispensing device 600 may include a user input device, such as a keyboard, a pointing device, etc.

In operation, a user may interact with the medication dispensing device 600, such as by using the display 610 (in the case of a touch screen or similar technology), or using a separate human input device, such as a keyboard or a pointing device. The drawers 620 of the medication dispensing device 600 may all be closed and/or locked when the user first interacts with the medication dispensing device 600. The user may provide login credentials to the medication dispensing device 600 and the medication dispensing device 600 may authenticate the user based on the credentials. The medication dispensing device 600 may then display a list of orders to the user, such as on the display. The orders displayed to the user may be determined based on the login credentials provided by the user. For example, the user may be associated with a particular area of a hospital and the orders displayed to the user may be for patients who are located in the area that of the hospital that is associated with the user.

The user may select a variable dose order from the list of displayed orders, such as by using the display 610 or a separate user input device. Upon receiving the user's selection, the medication dispensing device 600 may request that the user indicate the amount of the order that will be administered to the patient. The user may input the amount to be administered, the medication dispensing device 600 may verify that the amount is within a range of the variable dose order, and the medication dispensing device 600 may determine one or more items in inventory that contain the amount to be administered and minimize the amount that will be dispensed and/or wasted. The medication dispensing device 600 may open one or more drawers 620 storing one or more receptacles 630 that contain the determined one or more items. The medication dispensing device 600 may also open and/or release the one or more receptacles such that the user may access the items contained therein.

In one or more examples, the items contained in the receptacles 630 may each include an identifier, such as a bar code or a radio frequency identifier (RFID). The identifiers of the items may be used to ensure that the user does not retrieve more than the dispensed amount of an item from a receptacle 630, such as in instances when a receptacle 630 includes more than the dispensed amount of a particular item. For example, the medication dispensing device 600 may automatically track each item that is removed from a given receptacle based on the RFID of the removed items, and/or other item tracking mechanisms The medication dispensing device 600 may store an indication of the amount of the medication dispensed and the user identifier of the user to whom the medication was dispensed. If the amount of the medication dispensed exceeded the amount to be administered, the medication dispensing device 600 may display an indication of the excess amount of the medication that is to be wasted by the user, such as on the display 610. The medication dispensing device 600 may also display an amount of time that the user has to waste the excess amount before the excess amount will be identified as missing.

The medication dispensing device 600 may transmit to an external server, such as the management server 110, the identifier of the user, the amount dispensed, and the amount to be wasted, if any. The medication dispensing device 600 may also transmit the time allotted for wasting the excess amount to the external server if the time allotted was determined by the medication dispensing device 600.

Figure 7:
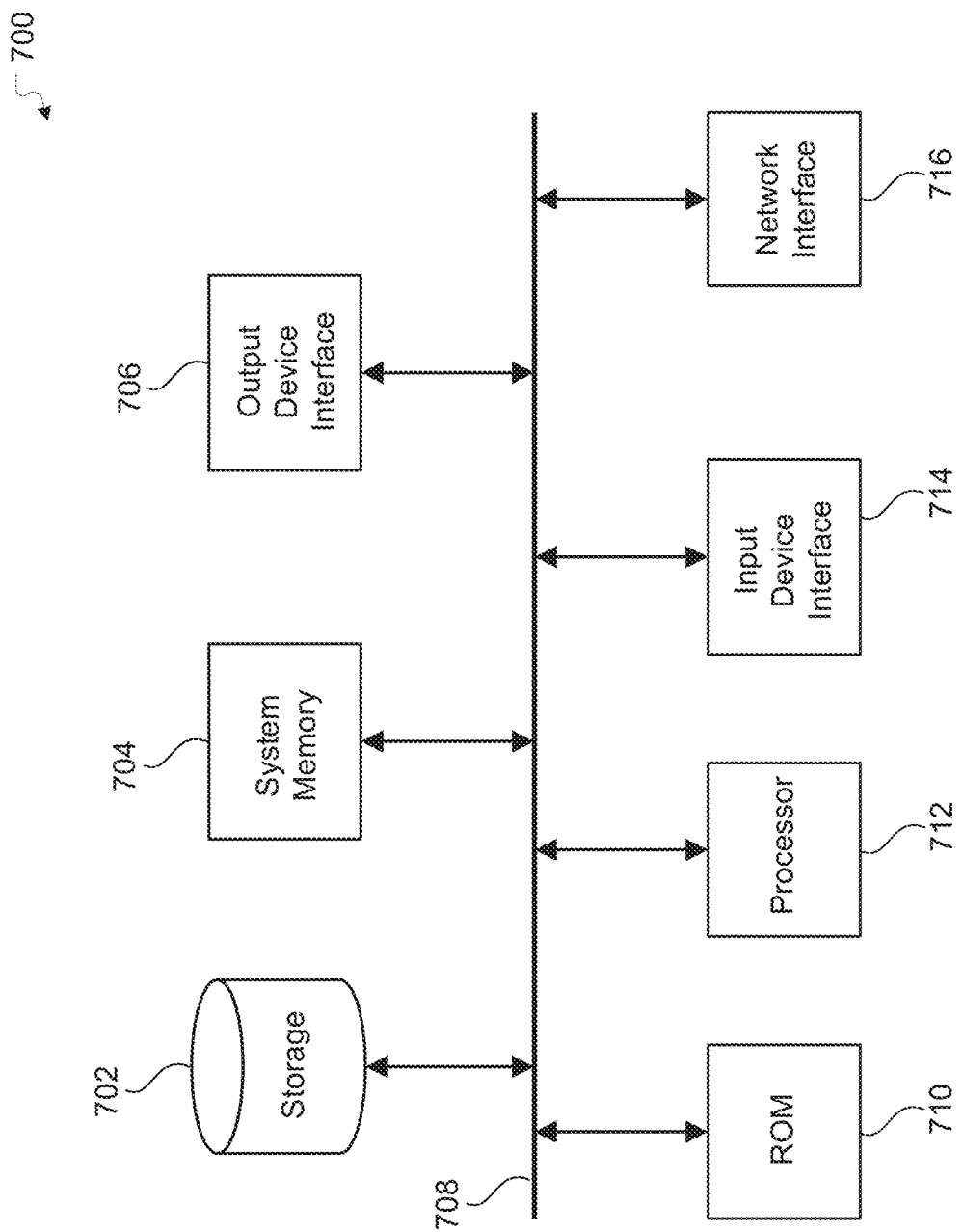
FIG. 7 conceptually illustrates an electronic system with which one or more embodiments of the subject technology may be implemented.

FIG. 7 conceptually illustrates electronic system 700 with which one or more embodiments of the subject technology may be implemented. Electronic system 700, for example, can be a medication dispensing device 140, a waste device 150, a server 110, 120, a desktop computer, a laptop computer, a tablet computer, a phone, a personal digital assistant (PDA), or generally any electronic device that transmits signals over a network. Such an electronic system includes various types of computer readable media and interfaces for various other types of computer readable media. Electronic system 700 includes bus 708, processing unit(s) 712, system memory 704, read-only memory (ROM) 710, permanent storage device 702, input device interface 714, output device interface 706, and network interface 716, or subsets and variations thereof.

Bus 708 collectively represents all system, peripheral, and chipset buses that communicatively connect the numerous internal devices of electronic system 700. In one or more embodiments, bus 708 communicatively connects processing unit(s) 712 with ROM 710, system memory 704, and permanent storage device 702. From these various memory units, processing unit(s) 712 retrieves instructions to execute and data to process in order to execute the processes of the subject disclosure. The processing unit(s) can be a single processor or a multi-core processor in different embodiments.

ROM 710 stores static data and instructions that are needed by processing unit(s) 712 and other modules of the electronic system. Permanent storage device 702, on the other hand, is a read-and-write memory device. This device is a non-volatile memory unit that stores instructions and data even when electronic system 700 is off. One or more embodiments of the subject disclosure use a mass-storage device (such as a magnetic or optical disk and its corresponding disk drive) as permanent storage device 702.

Other embodiments use a removable storage device (such as a floppy disk, flash drive, and its corresponding disk drive) as permanent storage device 702. Like permanent storage device 702, system memory 704 is a read-and-write memory device. However, unlike storage device 702, system memory 704 is a volatile read-and-write memory, such as random access memory. System memory 704 stores any of the instructions and data that processing unit(s) 712 needs at runtime. In one or more embodiments, the processes of the subject disclosure are stored in system memory 704, permanent storage device 702, and/or ROM 710. From these various memory units, processing unit(s) 712 retrieves instructions to execute and data to process in order to execute the processes of one or more embodiments.

Bus 708 also connects to input and output device interfaces 714 and 706. Input device interface 714 enables a user to communicate information and select commands to the electronic system. Input devices used with input device interface 714 include, for example, alphanumeric keyboards and pointing devices (also called "cursor control devices"). Output device interface 706 enables, for example, the display of images generated by electronic system 700. Output devices used with output device interface 706 include, for example, printers and display devices, such as a liquid crystal display (LCD), a light emitting diode (LED) display, an organic light emitting diode (OLED) display, a flexible display, a flat panel display, a solid state display, a projector, or any other device for outputting information. One or more embodiments may include devices that function as both input and output devices, such as a touchscreen. In these embodiments, feedback provided to the user can be any form of sensory feedback, such as visual feedback, auditory feedback, or tactile feedback; and input from the user can be received in any form, including acoustic, speech, or tactile input.

Finally, as shown in FIG. 7, bus 708 also couples electronic system 700 to a network (not shown) through network interface 716. In this manner, the computer can be a part of a network of computers (such as a local area network ("LAN"), a wide area network ("WAN"), or an Intranet, or a network of networks, such as the Internet. Any or all components of electronic system 700 can be used in conjunction with the subject disclosure.

Many of the above-described features and applications may be implemented as software processes that are specified as a set of instructions recorded on a computer readable storage medium (alternatively referred to as computer-readable media, machine-readable media, or machine-readable storage media). When these instructions are executed by one or more processing unit(s) (e.g., one or more processors, cores of processors, or other processing units), they cause the processing unit(s) to perform the actions indicated in the instructions. Examples of computer readable media include, but are not limited to, RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, ultra density optical discs, any other optical or magnetic media, and floppy disks. In one or more embodiments, the computer readable media does not include carrier waves and electronic signals passing wirelessly or over wired connections, or any other ephemeral signals. For example, the computer readable media may be entirely restricted to tangible, physical objects that store information in a form that is readable by a computer. In one or more embodiments, the computer readable media is non-transitory computer readable media, computer readable storage media, or non-transitory computer readable storage media.

In one or more embodiments, a computer program product (also known as a program, software, software application, script, or code) can be written in any form of programming language, including compiled or interpreted languages, declarative or procedural languages, and it can be deployed in any form, including as a stand alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

While the above discussion primarily refers to microprocessor or multi-core processors that execute software, one or more embodiments are performed by one or more integrated circuits, such as application specific integrated circuits (ASICs) or field programmable gate arrays (FPGAs). In one or more embodiments, such integrated circuits execute instructions that are stored on the circuit itself.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that any specific order or hierarchy of blocks in the processes disclosed is an illustration of example approaches. Based upon design preferences, it is understood that the specific order or hierarchy of blocks in the processes may be rearranged, or that all illustrated blocks be performed. Any of the blocks may be performed simultaneously. In one or more embodiments, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The predicate words "configured to", "operable to", and "programmed to" do not imply any particular tangible or intangible modification of a subject, but, rather, are intended to be used interchangeably. In one or more embodiments, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as an "aspect" may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as a "configuration" may refer to one or more configurations and vice versa.

The word "exemplary" is used herein to mean "serving as an example, instance, or illustration." Any embodiment described herein as "exemplary" or as an "example" is not necessarily to be construed as preferred or advantageous over other embodiments. Furthermore, to the extent that the term "include," "have," or the like is used in the description or the claims, such term is intended to be inclusive in a manner similar to the term "comprise" as "comprise" is interpreted when employed as a transitional word in a claim.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject disclosure.

What is claimed is:

1. A system for managing variable dose dispensing, the system comprising:
   one or more processors; and
   a memory including instructions that, when executed by the one or more processors, cause the one or more processors to:
   provide a list of formulary items;
   receive a selection of a first formulary item from the list;
   receive a first indication of an amount of a second formulary item from the list that is an equivalency to the first formulary item;
   store a first association between the amount of the second formulary item and the first formulary item;
   transmit the first association to a medication dispensing device;
   determine an amount of time to physically waste an excess amount of a dispensed medication of the first association to a user;
   detect expiration of the amount of time without receiving a notification of the physical wasting of the excess amount; and
   block access privileges of the user to the medication dispensing device.

2. The system of claim 1, wherein the instructions, when executed by the one or more processors, further cause the one or more processors to:
   receive a second indication of a variable dose group that is associated with the first formulary item;
   store a second association between the variable dose group and the first formulary item; and
   transmit the second association to the medication dispensing device.

3. The system of claim 2, wherein the instructions, when executed by the one or more processors, further cause the one or more processors to:
   transmit the first association to a waste device.

4. The system of claim 3, wherein the first formulary item and the second formulary item comprise different forms.

5. The system of claim 4, wherein the first formulary item comprises a tablet form and the second formulary item comprises a caplet form.

6. The system of claim 1, wherein the second formulary item has one of the same generic name as the first formulary item, an equivalency quantity below a threshold, and the same dosage as the first formulary item.

7. The system of claim 1, wherein the first formulary item is defined by a strength.

8. The system of claim 7, wherein the equivalency of the second formulary item is based on at least one of the strength of the first formulary item and the strength of the second formulary item.

9. The system of claim 7, wherein the equivalency of the second formulary item is based on whether the strength of the second formulary item is divisible by the strength of the first formulary item without resulting in fractional amounts.

10. The system of claim 7, wherein the equivalency of the second formulary item is based on at least one of the unit of measure of the first formulary item and the unit of measure of the second formulary item.

11. The system of claim 1, wherein if the first formulary item is defined by strength and total volume, the equivalency of the second formulary item is based on a derived concentration based on the defined strength and total volume.

12. The system of claim 1, wherein if the first formulary item is defined by a total volume, the equivalency of the second formulary item is based on a total volume of the second formulary item.

13. The system of claim 1, wherein if the first formulary item is defined by a total volume, the equivalency of the second formulary item is based on whether the volume amount of the second formulary item is divisible by the volume amount of the first formulary item without resulting in fractional amounts.

14. The system of claim 1, wherein if the first formulary item is defined by a concentration, the equivalency of the second formulary item is based on a concentration of the second formulary item.

15. The system of claim 1, wherein if the first formulary item is defined by a concentration, the equivalency of the second formulary item is based on whether a concentration strength of the second formulary item is divisible by a concentration strength of the first formulary item without resulting in fractional amounts.

16. The system of claim 1, wherein if the first formulary item is defined by a concentration, the equivalency of the second formulary item is based on having a concentration strength with one of the same unit of measure and the same configured base unit as the first formulary item.

17. The system of claim 1, wherein if the first formulary item is defined by a concentration, the equivalency of the second formulary item is based on having a concentration volume with the same internal volume as the first formulary item.

18. The system of claim 1, wherein the first formulary item is associated with a generic name and an amount of medication.

19. The system of claim 1, wherein the one or more processors are further caused to log the excess amount of the dispensed medication of the first association as undocumented when the excess amount is not physically wasted at the time the medication is removed from the medication dispensing device.

20. The system of claim 1, wherein, the determined amount of time is based on one of the dispensed medication, the dosage form of the dispensed medication, the manner in which the dispensed medication will be administered, and the condition of the patient receiving the dispensed medication.

* * * * *